United States Patent [19]
Hatori

[11] Patent Number: 4,805,596
[45] Date of Patent: Feb. 21, 1989

[54] ENDOSCOPE

[75] Inventor: Tsuruo Hatori, Tokyo, Japan

[73] Assignee: Olympus Optical Co., Ltd., Tokyo, Japan

[21] Appl. No.: 174,116

[22] Filed: Mar. 28, 1988

[30] Foreign Application Priority Data

Apr. 3, 1987 [JP] Japan .................................. 62-82626

[51] Int. Cl.⁴ .............................................. A61B 1/00
[52] U.S. Cl. ...................................................... 128/4
[58] Field of Search ........................ 128/3, 4, 5, 6, 7, 8

[56] References Cited

U.S. PATENT DOCUMENTS

| | | | |
|---|---|---|---|
| 3,091,235 | 5/1963 | Richards | 128/6 |
| 3,583,393 | 6/1971 | Takahashi | 128/4 |
| 3,788,304 | 1/1974 | Takahashi | 128/6 |
| 4,327,711 | 5/1982 | Takagi | 128/4 |

FOREIGN PATENT DOCUMENTS 37-85214 6/1962 Japan .
59-69024 4/1984 Japan .

Primary Examiner—William H. Grieb
Attorney, Agent, or Firm—Ladas & Parry

[57] ABSTRACT

An endoscope has an operating section and an insertion section. The insertion section includes a flexible tube and a bending tube. At least two wires for operating the bending tube from the operating section are each connected at one end to the bending tube, with at least two wire guides for guiding these wires being arranged in the flexible tube. The endoscope further includes a coupling member for coupling the flexible tube and the bending tube to each other. The coupling member consists of at least two parts which can be combined integral, and one of the wire guides is fixed to each of the parts.

6 Claims, 6 Drawing Sheets

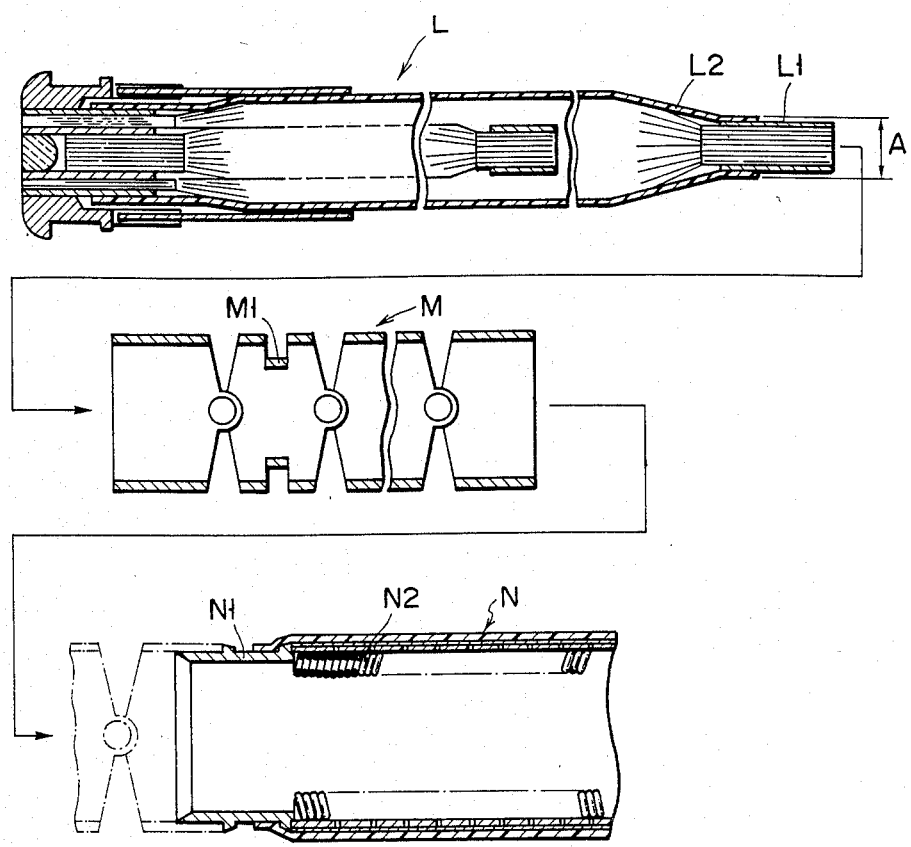
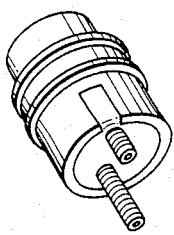
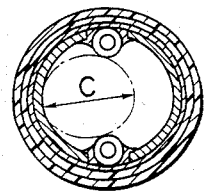
PRIOR ART
FIG. 1
PRIOR ART
FIG. 2
PRIOR ART
FIG. 3

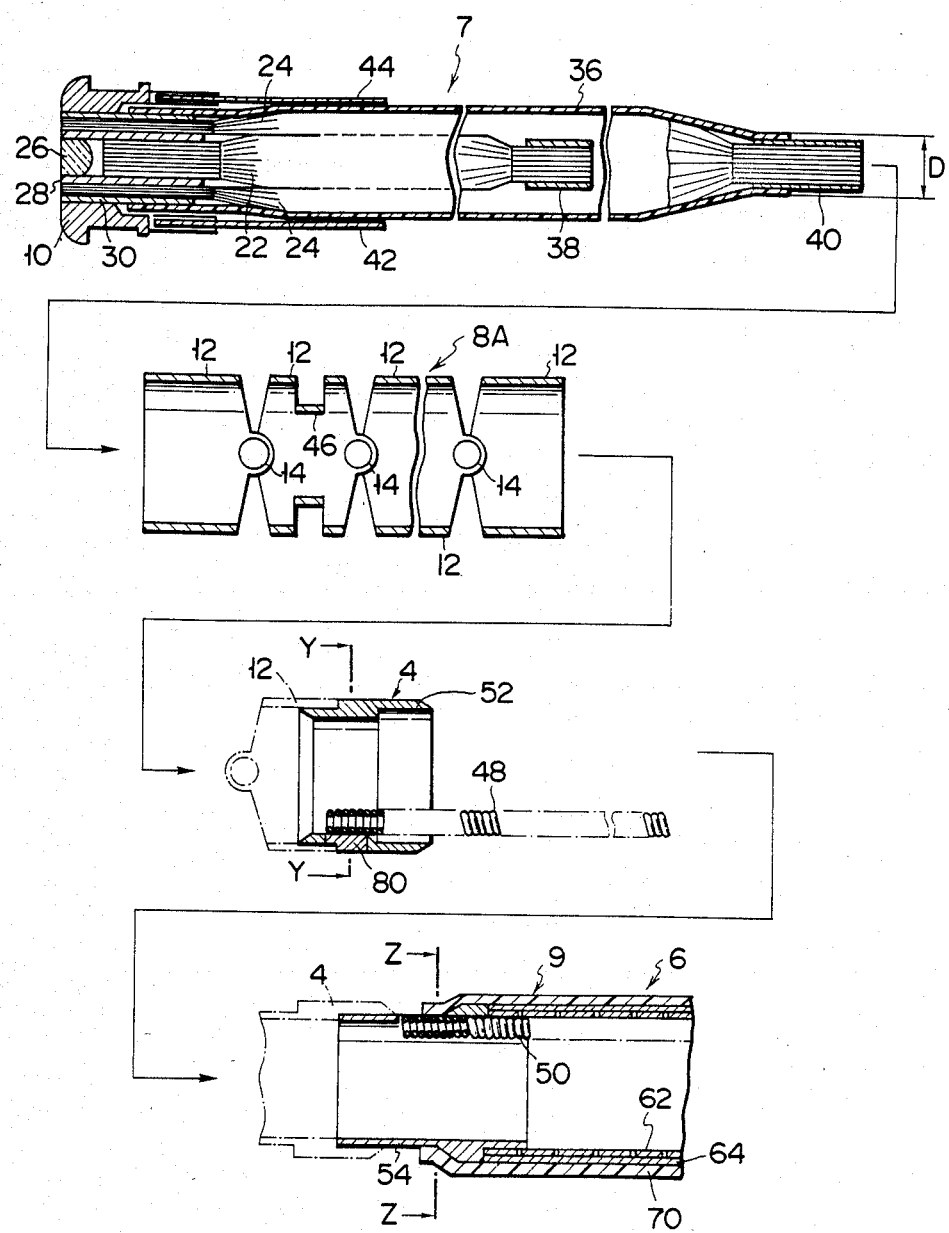
F I G. 9

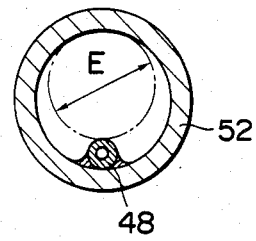
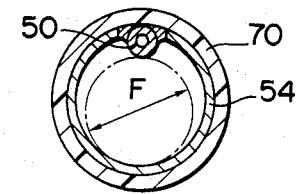
FIG. 10    FIG. 11
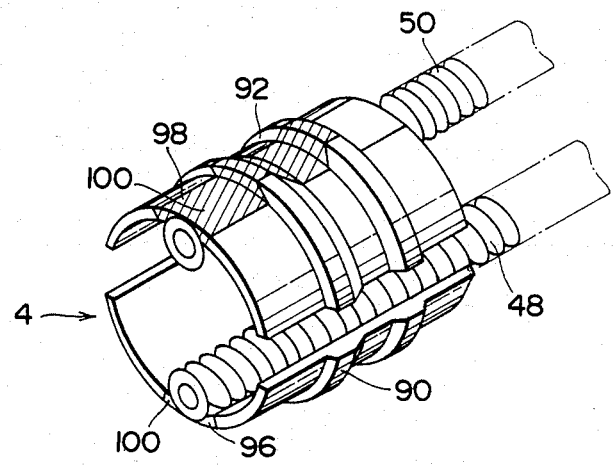
FIG. 12

ENDOSCOPE

BACKGROUND OF THE INVENTION

1. Field of the Invention

The present invention relates to a structure for attaching wire guides which guide operation wires incorporated in the insertion section of an endoscope and, more particularly, to an endoscope provided with an improved structure for attaching the wire guides.

2. Description of the Related Art

A typical endoscope includes an operating section, an insertion section which is inserted into a cavity of the human body, a light guide cable connected to the operating section, and a light source connector section for connecting the light guide cable to an illuminating light source means.

Wires for causing the foremost end portion of the insertion section to bend and wire guides for guiding these wires are arranged inside the insertion section of the endoscope. A typical wire guide attaching structure is disclosed in, for example, Japanese Patent Disclosure (Koki) No. 59-69024.

The process of assembling the insertion section of a typical endoscope will now be described, with reference to FIGS. 1 through 3. As is shown in FIG. 1, the insertion section is made up of three separate units which are subsequently assembled into a single piece. First unit L has a housing which forms the distal end of the insertion section and to which are attached image and light guide fibers, an objective lens system, operating wires and so forth. Cap member L1, mounted on the base end portion of the light guide fiber handle of first unit L, is inserted into second unit M (or bending tube having wire guide rings M1), followed by the body of first unit L. In addition, cap member L1 of first unit L is inserted into third unit N (or flexible tube portion), again followed by the body of first unit L. Finally, the first, second, and third units are joined together, being secured to one another by means of a bonding agent or the like.

When the above-described assembly process has been completed, coating tube L2 is attached round cap member L1. Diameter A which is obtained by adding the thickness of coating tube L2 to the outer diameter of cap member L1 must be made smaller than the inner diameter of the guide ring portion of the bending tube. In addition, it must be made smaller than the smallest inner diameter C at coupling tube N1 where the bending and flexible tubes of the insertion section are connected to each other, particularly at that portion of the insertion section to which wire guides N2 are attached in FIG. 3. Therefore, the cap member must be smaller than the smallest inner diameter of the insertion section of the endoscope.

Cap member L1 is hard and cannot be deformed in its radial direction, but the other portion of the internal matters which is coated by coating tube L2 is soft and can be deformed in its radial direction. If the hard portion of first unit L which has diameter A can be inserted into second and third units, the insertion section can be assembled. Therefore, that portion of third unit N which has the smallest diameter C, as shown in FIG. 3, is important. As shown in FIG. 2, the foremost end of the wire guides are fitted into cut-away slits in coupling tube N1 at that portion of third unit N and fixed there by filling a bonding agent in the slit.

When the insertion section of the endoscope which is assembled according to the above-described process is to be made still smaller in its outer diameter, the wire guides must be made still slimmer. However, they need to have such a strength that they cannot be deformed by the pulling force of the operating wire, and they must be made thick to some extent accordingly. Therefore, there is a limit in making them slimmer.

This asks that the wire guide attaching structure is improved in order to make the insertion section of the endoscope smaller in its outer diameter.

SUMMARY OF THE INVENTION

The object of the present invention is to provide an endoscope having an insertion section whose outer diameter can be made smaller by an improved structure for attaching wire guides which guide operating wires.

This object of the present invention can be achieved by an endoscope arranged as follows:

The endoscope according to the invention has an operating section and an insertion section, the body of the insertion section being constituted by a flexible tube, the foremost end thereof being a bedding tube. At least two wires for operating the bending tube from an operating section of the endoscope are each connected at one end to the bending tube, with at least two wire guides for guiding these wires being arranged in the flexible tube. The endoscope also includes a coupling member for coupling the flexible and bending tubes to each other, and this coupling member includes at least two parts which can be assembled integral and to each of which is fixed one of the wire guides.

According to the present invention, the coupling member for coupling the flexible and bending tubes to each other is divided to two or more parts, to each of which one of the wire guides is fixed. When the endoscope is to be assembled, therefore, a cap member mounted on a base end portion of an optical fiber bundle can be easily inserted into the inner hole of the coupling member even if the diameter of this inner hole of the coupling member is relatively small. The outer diameter of the insertion section can be thus made still smaller. In addition, internal matters can be filled at a higher density in the inner space of the insertion section which has a certain outer diameter. For example, the number of optical fibers which are the internal matters can be increased and an outer diameter of each of some channels for treating tools can be made larger.

BRIEF DESCRIPTION OF THE DRAWINGS

FIGS. 1 through 3 are vertically-sectioned, perspective and cross-sectioned views showing the conventional endoscope;

FIG. 9 is a sectional view showing each of units in the process of assembling the insertion section of the endoscope;

FIG. 10 is a sectional view taken along a line Y—Y in FIG. 9;

FIG. 11 is a sectional view taken along a line Z—Z in FIG. 9; and

FIG. 12 is a perspective view showing a coupling member employed by a second embodiment of the endoscope according to the present invention.

DETAILED DESCRIPTION OF THE PREFERRED EMBODIMENTS

Some embodiments of the endoscope according to the present invention will be described with reference to the drawings.

Figure 4:
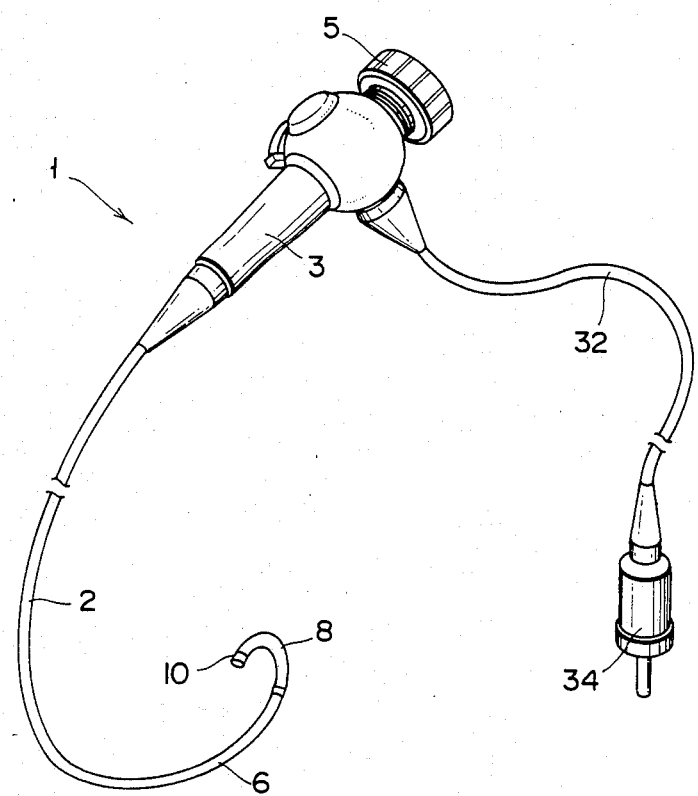
FIG. 4 is a perspective view showing the whole of an endoscope according to the present invention.

FIGS. 4 through 9 show a first embodiment of the endoscope according to the present invention. Endoscope 1 shown in FIG. 4 is provided with insertion section 2 comprising flexible tube portion 6, bending tube portion 8 and distal end member 10, and operating section 3 is conneted to the proximal end of inserted section 2. Light guide cable 32 is connected to operating section 3 and light source connector 34 is attached to the distal end of cable 32. Operating section 3 is also provided with eyepiece portion 5.

Figure 5:
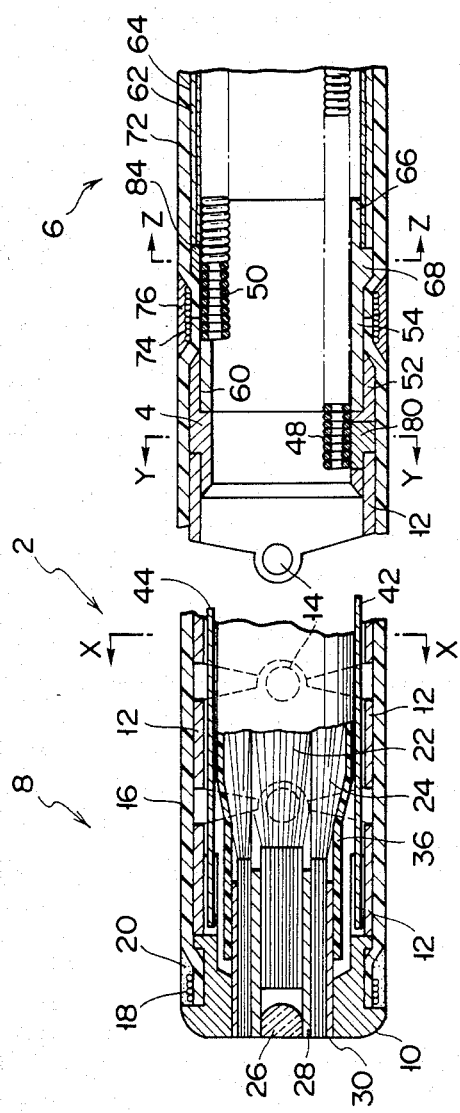
FIG. 5 is a vertically-sectioned view showing an insertion section of the first embodiment of the endoscope according to the present invention.

As shown in FIG. 5, flexible tube portion 6 and bending tube portion 8 are connected to each other through coupling tube 4, which serves as a coupling member, at insertion section 2 of the endoscope and a distal end member or housing 10 is coupled to the distal end of bending tube portion 8. A plurality of tubular segments 12 are arranged in a line at bending tube portion 8 and in the axial direction of bending tube portion 8 and adjacent tubular segments 12 are linked by pins 14 to be curved up and down. The outer circumferences of these tubular segments 12 are covered by outer sheath tube 16. The distal end of this outer sheath tube 16 is extended onto the outer circumference of the rear portion of housing 10 and fixed there by threads 18 and bonding agent 20.

The distal end portions of image and light guide fiber bundles 22 and 24 which are inserted through insertion section 2 are attached to housing 10. More specifically, the distal end portion of image guide fiber bundle 22 is located and folded in housing 10 behind objective lens 26 by means of image guide fiber cap 28, while that of light guide fiber bundle 24 is sandwiched like a hollow cylinder between image and light guide fiber caps 28 and 30 inserted and folded in the fore of housing 10. Image guide fiber bundle 22 which is arranged in the hole of light guide fiber bundle 24 is extended to eyepiece portion 5 in operating section 3 and its base end portion is fixed to eyepiece portion 5 by cap member 38 mounted on the base end portion. Light guide fiber bundle 24 is extended to light source connector 34 at the foremost end of light guide cable 32, passing through operating section 3 and light guide cable 32, and its base end portion is fixed to light source connector 34 by cap member 40 mounted on base end portion. Image and light guide fiber bundles 22 and 24 are housed in coating tube 36 at insertion section 2 but they are separated from each other and housed in different coating tubes (not shown) at operating section 3.

Figure 6:
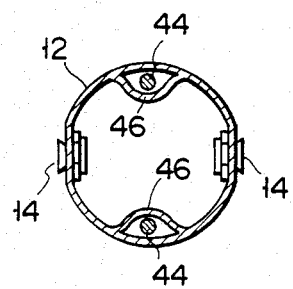
FIG. 6 is a sectional view taken along a line X—X in FIG. 5.

Foremost tubular segment 12 is coupled to the rear end portion of housing 10 which is located on the distal end portion of the endoscope, and bonded or soldered there by bonding agent or the like. The foremost ends of bending operation wires 42 and 44 are connected to the upper and lower inner faces of foremost tubular segment 12. Bending operation wires 42 and 44 are arranged along the upper and lower inner faces of insertion section 2 and they are guided in bending tube 8 by guide rings 46 formed on the inner face of tubular segments 12, as shown in FIG. 6, while they are guided in flexible tube 6 by first and second wire guides 48 and 50.

Figure 7:
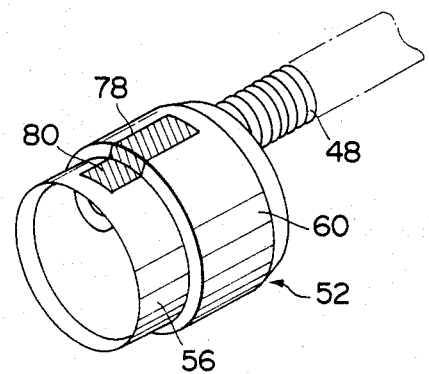
FIGS. 7 and 8 are perspective views showing a coupling member employed by the first embodiment of the endoscope.
Figure 8:
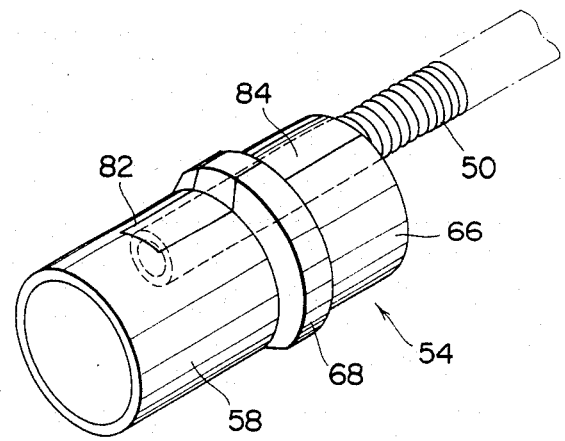

Coupling means 4 employed by the first embodiment of the endoscope consists of first connector tube 52 shown in FIG. 7 and second connector tube 54 shown in FIG. 8. The foremost end of first connector tube 52 is provided with small-diameter portion 56 which is inserted into the inner hole of rearmost tubular segment 12 in bending tube portion 8. The rear end of first connector tube 52 is provided with large diameter portion (or rear end portion) 60 which houses small-diameter portion (or front end portion) 58 of second connector tube 54. The rear end portion of second connector tube 54 is provided with small diameter portion 66 which is inserted into spiral tube 62, which serves as a core member, and also into tubular braid 64. The intermediate portion of second connector 54 is formed like ring-shaped collar 68.

As shown in FIG. 5, first and second connector tubes 52 and 54 are coupled to each other and tubular segment 12 and first connector tube 52 are coupled to each other. Intermediate collar 68, rear end portion 60 of first connector tube 52 and tubular segment 12 form a flat outer circumference in this case because they have same outer diameter. Outer sheath tube 16 of bending tube portion 8 and that of flexible tube portion 6 are met each other in a ring-shaped groove formed between rear end portion 60 of first connector tube 52 and collar 68 of second connector tube 54, and they are fastened by threads 74 and then bonded there by bonding agent 76.

First cut-away slit 78 which is opened upward is formed in first connector tube 52 and partly overlapped by rearmost tubular segment 12 which is coupled to small diameter portion 56, slit 78 extending over small diameter portion 56 and rear end portion 60. Tubular segment 12 and connector tube 52 are fixed to each other by bonding means 80 such as the bonding agent or soldering material supplying into cut-away slit 78.

First operating wire 42 is inserted into first wire guide 48 fixed to first connector tube 52, while second operating wire 44 into second wire guide 50 fixed to second connector tube 54. As shown in FIG. 6, operating wires 42 and 44 in bending tube portion 8 are inserted into guide rings 46 formed on the inner face of tubular segment 12 and their proximal ends are connected to a bending operation mechanism (not shown) arranged at operating section 3.

As shown in FIG. 7, first connector tube 52 and wire guide 48 are fixedly bonded together with rearmost tubular segment 12 by filling cut-away slit 78 with fixing means 80 such as bonding agent or the like. Fixing means 80 is filled in slit 78 in such a way that it is not projected from the outer surface of first connector tube 52.

Second connector tube 54 and wire guide 50 are connected to each other in same way as seen in the case of first connector tube 52. As shown in FIG. 8, cut-away slit 82 is formed in the rear portion of second connector tube 54 in the axial direction thereof and second wire guide 50 is held in cut-away slit 82 and fixedly bonded there by fixing means 84, which fills cut-away slit 82 in this case not to project from the outer surface of second connector tube 54.

The process of assembling insertion section of the endoscope according to the present invention will be described with reference to FIG. 9. As shown in FIG. 9, cap member 40 of first unit 7, which is mounted on the base end portion of the light guide fiber bundle 24 and partly coated by coating tube 36, is inserted into bending tube 8A and the body of first unit 7 is then inserted. At the same time, operating wires 42 and 44 are also inserted into guide rings 46. Cap member 40 of first unit 7 is inserted into first connector tube 52 which is provided with first wire guide 48. First operating wire 42 is also inserted into first wire guide 48 this time. Cap member 40 mounted on the base end portion of the light guide fiber bundle 24 is inserted into second unit 9 and second operating wire 44 is inserted into second wie guide 50 at the same time. Second unit 9 includes second connector tube 54 provided with second wire guide 50, and flexible tube portion 6 previously connected to second connector tube 54. First and second connector tubes 52 and 54 are coupled to each other after cap member 40 of first unit 7 is passed through them.

The internal matters such as the optical fibers which are arranged in first unit 7 from cap member 40 to the foremost end thereof are soft. When hard cap 40 of first unit 7 is passed through first and second connector tubes 52 and 54 in the process of combining first, second and third units, therefore, the inserted section can be easily assembled.

It is determined only by the inner diameter of first connector tube 52 and the outer diameter of first wire guide 48, as shown in FIG. 10, whether or not cap member 40 mounted on the base end portion of light guide fiber bundle 24 can pass through first connector tube 52. It is also determined only by the inner diameter of second connector tube 54, depth of cut-away slit 82 (or thickness of second connector tube 54) and outer diameter of second wire guide 50, as shown in FIG. 11, whether or not cap member 40 of first unit 7 can pass through second connector tube 54.

If the outer diameter of insertion section 2 of the endoscope according to the present invention is equal to that of the insertion section of the conventional endoscope, therefore, "diameter C of a virtual circle<diameter E" and "diameter C<diameter E" will be established and the cross sectional area of the internal matters such as the optical fibers in insertion section 2 can be increased. Alternatively, when outer diameter A of the internal matters of the conventional endoscope equals to outer diameter D of that of this invention, the outer diameter of insertion section 2 can be made smaller.

FIG. 12 shows a second embodiment of the present invention. Coupling tube 4 is divided into first and second coupling tube halves 90 and 92 in the radial direction thereof. Coupling tube 4 is formed by combining these two parts. First and second coupling tube halves 90 and 92 are provided with cut-away slits 96 and 98, in which first and second wire guides 48 and 50 are located and fixedly bonded by fixing means 100.

The insertion section of the second embodiment can be assembled similarly to the case of the first embodiment. However, it is needed that first and second coupling tube halves 90 and 92 are combined with each other after cap member 40 mounted on the base end portion of the light guide fiber bundle is passed between them. It is also needed that wire guides 48 and 50 are mounted on coupling tube halves 90 and 92 by fixing means 10 to keep their inside waterproof.

Coupling tube 4 can be made shorter in the second embodiment of this invention because coupling tube 4 is divided into two parts in the radial direction thereof. Namely, the hard portion for connecting bending tube portion 8 and flexible tube portion 6 to each other can be made shorter.

Although the endoscope whose bending tube is operated by two operating wires has been described in the case of the first and second embodiments of the present invention, the coupling tube of the present invention may be applied to an endoscope wherein the number of operating wires is increased and the constitution of the bending tube is modified to bend in two or more directions. Further, the coupling tube may consist of three or more parts.

Although only the optical fibers has been shown as the internal matters in the insertion section in the case of the first and second embodiments, those channel tubes through which liquid such as medicine can be injected into the human body, dirt and the like can be sucked, and treating tools can be passed may be provided as well.

What is claimed is:
1. An endoscope comprising:
an operating section; and
an insertion section connected to said operating section and having a flexible tube which forms the body of said insertion section, a bending tube which forms the distal end portion of said insertion section, at least two wire means for operating said bending tube from the operating section, one end of each of said wire means being connected to said bending tube, at least two wire guide means arranged in said flexible tube and serving to guide said wire means, and a coupling means for coupling the flexible tube and the bending tube to each other, said coupling means including at least two parts which can be combined integral, and one of the wire guide means being fixed to each of said parts.

2. The endoscope according to claim 1, wherein said coupling means comprises two tubular members which can be coupled to each other in the longitudinal direction thereof.

3. The endoscope according to claim 2, wherein said tubular members are provided with cut-away slits in which said wire guide means are located and which are filled with fixing means.

4. The endoscope according to claim 1, wherein said coupling means comprises a tubular member which is divided into two portions in the radial direction thereof.

5. The endoscope according to claim 2, wherein said two portions are provided with cut-away slits in which said wire guide means are located and which are filled with fixing means.

6. The endoscope according to claim 1, wherein said wire guide means are spiral springs.

* * * * *